United States Patent [19]
Truwit et al.

[11] Patent Number: 5,964,705
[45] Date of Patent: Oct. 12, 1999

[54] MR-COMPATIBLE MEDICAL DEVICES

[75] Inventors: Charles L. Truwit, Wayzata; Haiying Liu, Minneapolis, both of Minn.

[73] Assignee: Image-Guided Drug Delivery System, Inc., Minneapolis, Minn.

[21] Appl. No.: 08/916,596

[22] Filed: Aug. 22, 1997

[51] Int. Cl.[6] .......................... A61B 5/055; G01R 33/00
[52] U.S. Cl. .......................... 600/423; 600/13; 324/318
[58] Field of Search .................... 600/423, 422, 600/424, 11, 12, 13; 128/899, 903; 604/20; 324/318, 322

[56] References Cited

U.S. PATENT DOCUMENTS

| | | | |
|---|---|---|---|
| 4,572,198 | 2/1986 | Codrington | 128/653 |
| 4,767,973 | 8/1988 | Jacobsen et al. | 318/652 |
| 4,827,931 | 5/1989 | Longmore | 128/334 R |
| 5,106,455 | 4/1992 | Jacobsen et al. | 156/659.1 |
| 5,154,179 | 10/1992 | Ratner | 128/653.4 |
| 5,167,625 | 12/1992 | Jacobsen et al. | 604/891.1 |
| 5,180,982 | 1/1993 | Zeiger | 324/322 |
| 5,211,165 | 5/1993 | Dumoulin et al. | 128/653.1 |
| 5,269,882 | 12/1993 | Jacobsen | 156/659.1 |
| 5,270,485 | 12/1993 | Jacobsen | 174/15.1 |
| 5,271,400 | 12/1993 | Dumoulin et al. | 128/653.2 |
| 5,273,622 | 12/1993 | Jacobsen | 156/659.1 |
| 5,375,596 | 12/1994 | Twiss et al. | 128/653.1 |
| 5,451,744 | 9/1995 | Koopman et al. | 219/400 |

FOREIGN PATENT DOCUMENTS

| | | | |
|---|---|---|---|
| 93/15785 | 2/1993 | WIPO | A61M 25/00 |
| 93/15872 | 2/1993 | WIPO | B23P 17/00 |
| 93/15874 | 8/1993 | WIPO | B23Q 7/04 |
| 94/27697 | 5/1994 | WIPO | A65M 25/00 |
| 96/33761 | 4/1996 | WIPO | A61M 25/00 |

OTHER PUBLICATIONS

Turner, R., "Minimum Inductane Coils", *J. Phys. E. Sci. Instrum*, vol. 21, pp. 948–952, (1988).

(List continued on next page.)

Primary Examiner—William E. Kamm
Assistant Examiner—Shawna J Shaw
Attorney, Agent, or Firm—Schwegman, Lundberg, Woessner & Kluth PA

[57] ABSTRACT

The use of devices in procedures, especially medical procedures where the events take place under view of Magnetic Resonance Imaging (MRI) systems is becoming more important. Although some general and specific structures have been discussed in the literature and commercialized, little has been done effectively to design devices for MRI procedures for specific tasks. The present invention describes a device for use within an organism, said device comprising an element having at least one pair of opposed RF receiver microcoils having a space between each microcoil of said pair of microcoils, the coils of said microcoils may have diameters of less than 2.4 mm. The device may also comprise an element having at least one pair of opposed RF receiver microcoils having a space between each microcoil of said pair of microcoils, said RF receiver microcoils each comprising at least three individual coils, said at least three individual coils of said microcoils having spacing between adjacent microcoils so that spacing between at least two pairs of individual coils within said microcoils differ by at least 10%. Circuitry may be insulated within the device by providing the wires and circuits within different layers in a coaxial layering of components within the catheter. The device may also comprise device an element having at least one pair of opposed RF receiver microcoils having a space between each microcoil of said pair of microcoils, the RF receiver microcoils each comprising at least three individual windings, the at least three individual windings of said microcoils having spacing between adjacent windings so that spacing between at least two pairs of individual windings within the microcoils differ by at least 10%.

20 Claims, 5 Drawing Sheets

OTHER PUBLICATIONS

Coutts, G.A., et al., "Integrated position tracking and imaging of interventional tools and internal devices using small fiducial receiver coils", *Proceedings of the International Society for Magnetic Resonance in Medicine, Fifth Scientific Meeting and Exhibition, Vancouver, BC, Canada,* vol. 3, p. 1924, (Apr. 12–18, 1997).

Erhart, P., et al., "Tissue independent tracking of biopsy needles with an internal signal source", 1740.

Gohde, S.C., et al., "MR–guided cholecystostomy in a pig: assessment of biplanar, real–time Needle Tracking", Proceedings of the International Society for Magnetic Resonance in Medicine, Fourth Scientific Meeting and Exhibition, New York, USA, vol. 2, p. 892, (Apr. 27–May 3, 19).

Hurst, G.C., et al., "Intravascular (Catheter) NMR Receiver Probe: Preliminary Design Analysis and Application to Canine Iliofemoral Imaging", *Magnetic Resonance in Medicine,* vol. 24, No. 2, pp. 343–357, (1992).

Martin, A.J., et al., "MR Imaging of Blood Vessels with an Intravascular Coil", *J. Mag. Res. Imag., 2, No. 4,* 421–429, (1992).

MR-COMPATIBLE MEDICAL DEVICES

BACKGROUND OF THE INVENTION

1. Field of the Invention

The present invention relates to medical devices which are compatible with procedures performed during magnetic resonance imaging (MRI), and particularly to medical devices which can deliver drugs during procedures viewed with magnetic resonance (MR) imaging techniques.

2. Background of the Art

Medical procedures may now be performed on areas of the patient which are relatively small. Procedures may be performed on small clusters of cells, within veins and arteries, and in remote sections of the body with minimally invasive techniques, such as without surgical opening of the body. As these procedures, such as balloon angioplasty, microsurgery, electrotherapy, and drug delivery are performed within the patient with minimally invasive techniques without major surgical opening of the patient, techniques have had to be developed which allow for viewing of the procedure concurrent with the procedure. X-ray imaging, such as X-ray fluoroscopy, is a possible method of providing a view of the procedural area, but X-ray exposure for any extended period of time is itself harmful to the patient. Fiber optic viewing of the area does not provide any harmful radiation to the patient, but the fiber optics may take up too large a space to provide both the light necessary for viewing and a path for return of the light, and does not permit beyond the surface imaging (that is, only the surfaces of internal objects may be viewed from the position where the fiber optic device is located). Fiber optics or direct light viewing is more acceptable for larger area medical procedures such as gastroenterological procedures than for more microscopic procedures such as intraparenchymal drug delivery or endovascular drug delivery or procedures.

Techniques have been developed for relatively larger area viewing of MR-compatible devices within a patient by the use of MR-receiver coils in the devices which are tracked by MR imaging systems. Little by way of specific design considerations have been given to devices which have MR viewing capability and specific treatment functions, and especially where the relationship of specific types of treatment and the MR receiver coils must be optimized both for a treatment process and for MR viewing ability.

U.S. Pat. No. 5,211,165 describes a tracking system to follow the position and orientation of an invasive device, and especially a medical device such as a catheter, using radio frequency field gradients. Detection of radio frequency signals is accomplished with coils having sensitivity profiles which vary approximately linearly with position. The invasive device has a transmit coil attached near its end and is driven by a low power RF source to produce a dipole electromagnetic field that can be detected by an array of receive coils distributed around an area of interest of the subject. This system places the transmit coils within the subject and surrounds the subject with receive coils.

U.S. Pat. No. 5,271,400 describes a tracking system to monitor the position and orientation of an invasive device within a subject. The device has an MR active sample and a receiver coil which is sensitive to magnetic resonance signals generated by the MR active sample. These signals are detected in the presence of magnetic field gradients and thus have frequencies which are substantially proportional to the location of the coil along the direction of the applied gradient. Signals are detected responsive to sequentially applied mutually orthogonal magnetic gradients to determine the device's position in several dimensions. The invasive devices shown in FIGS. 2a and 2b and rf coil and an MR active sample incorporated into a medical device and an MR active sample incorporated into a medical device, respectively.

U.S. Pat. No. 5,375,596 describes a method and apparatus for determining the position of devices such as catheters, tubes, placement guidewires and implantable ports within biological tissue. The devices may contain a transmitter/detector unit having an alternating current radio-frequency transmitter with antenna and a radio signal transmitter situated long the full length of the device. The antennae are connected by a removable clip to a wide band radio frequency (RF) detection circuit, situated within the transmitter/detector unit.

U.S. Pat. No. 4,572,198 describes a catheter for use with NMR imaging systems, the catheter including a coil winding for exciting a weak magnetic field at the tip of the catheter. A loop connecting two conductors supports a dipole magnetic field which locally distorts the NMR image, providing an image cursor on the magnetic resonance imaging display.

U.S. Pat. No. 4,767,973 describes systems and methods for sensing and movement of an object in multiple degrees of freedom. The sensor system comprises at least one field-effect transistor having a geometric configuration selected to provide desired sensitivity.

Published PCT Applications WO 93/15872, WO 93/15874, WO 93/15785, and WO 94/27697 show methods of forming tubing, including kink resistant tubing and catheters in which the catheters may contain reinforcing coils. Layer(s) of reinforcing materials may be deposited on and over the reinforcing coils.

U.S. Patent Nos. 5,451,774 and 5,270,485 describes a three-dimensional circuit structure including a plurality of elongate substrates positioned in parallel and in contact with each other. Electrical components are formed on the surfaces of the substrates, along with electrical conductors coupled to those components. The conductors are selectively positioned on each substrate so as to contact conductors on adjacent substrates. The conductor patterns on the substrates may be helical, circumferential, or longitudinal. Radio frequency signaling between substrates would be effected with a transmitting antenna and a receiving antenna, with radio frequency signal transmitting and receiving circuitry present in the substrates (e.g., column 7, lines 32–43). Circulation of cooling fluid within the device is shown.

U.S. Pat. No. 5,273,622 describes a system for the fabrication of microstructures (including electronic microcircuitry) and thin-film semiconductors on substrates, especially continuous processes for use on elongate substrates such as fibers or filaments.

U.S. Pat. Nos. 5,106,455 and 5,269,882 describes a method and apparatus for fabrication of thin film semiconductor devices using non-planar exposure beam lithography. Circuitry formed on cylindrical objects is shown.

U.S. Pat. No. 5,167,625 describes a multiple vesicle implantable drug delivery system which may contain an electrical circuit which is responsive to signals (including radio signals) which can be used to effect drug delivery.

PCT Application WO 96/33761 (filed Apr. 15, 1996) describes an intraparenchymal infusion catheter system for delivering drugs or other agents comprising a pump coupled to the catheter. A porous tip is disposed at a distal end of the catheter, the tip being porous to discharge an agent or rug at a selected site. The catheter may be customized during use by an expandable portion of the catheter system.

Martin, A. J., Plewes, D. B. and Henkelman, R. M. in "MR Imaging of Blood Vessels with an Intravascular Coil," J. Mag. Res. Imag., 1992, 2, No.4, pp. 421–429 describes a method for producing high-resolution magnetic resonance (MR) images of blood vessel walls using a theoretic receiver-coil design based on two coaxial solenoids separated by a gap region and with the current driven in opposite directions. The coils had diameters ranging from 3 to 9 mm. FIG. 3b appears to indicate that sensitivity decreases as the coils diameter moved from 9 to 7 to 5 to 3 mm. Investigation of the Q value of opposed loop and opposed solenoid coils indicated that opposed loop coils displayed low W values and that there was a general trend of lower Q values at smaller Q diameters among the opposed solenoid designs. Within the range investigated, it was stated that a compromise exists between the use of thicker wire for improved performance and thinner wire to limit the overall coil dimensions. Decoupling circuitry is also shown to be useful in performing the imaging functions with this catheter based system in MR imaging.

Hurst, G. C., Hua, J., Duerk, J. I. and Choen, A. M., "Intravascular (Catheter) NMR Receiver Probe: Preliminary Design Analysis and Application in Canine Iliofemoral Imaging," Magn. Res. In Imaging, 24, 343–357 (1992) explores the feasibility of a catheter-based receiver probe for NMR study of arterial walls. Various potential designs, including opposed solenoids (e.g., FIG. 2b and FIG. 3 a and b) are examined. The catheter probe shown in FIG. 3 was constructed with five turns of 28 gauge wire per solenoid, with 7.5 mm between solenoids and nominal solenoid diameters of 2.8 mm, with the probe resonating at 64 MHz with a 110-pf capacitor.

SUMMARY OF THE INVENTION

A device is described for use within an organism, said device may comprise an element having at least one pair of opposed RF receiver microcoils having a space between each microcoil of said pair of microcoils, the coils of said microcoils having diameters which may be of any useful size, e.g., 3 mm, 4 mm or more, but in many preferred systems may be less than 2.4 mm or less than 2.6 mm. The device may comprise a catheter having at least one lumen, where the at least one pair of microcoils is radially located about the at least one lumen and the coils have diameters of greater than 0.1 mm and less than 2.4 mm, although larger diameter wires in the coils may be used. The device may have no ports or at least one drug delivery port present within said device. The least one drug delivery port may be located so that at least some drug which is delivered through said port is delivered away from said device within said space between said microcoils. The delivery ports may comprise microcatheters present within said device which extend outside of said device to deliver at least some liquid material within a volume bordered by planes extending radially from the catheter at ends of the at least one pair of microcoils which define the space between each microcoil within said at least one pair of microcoils. The device, in response to radio frequency transmission, may generate a field which has an average strength within said volume greater than in comparable size volumes surrounding said catheter which are radially located directly over each of said microcoils. The at least one pair of microcoils preferably is embedded within a binder material which surrounds said lumen. The at least one pair of microcoils is electrically connected to a preamplifier within a portion of said device which may be inserted into an organism. Where electrical connections are present within said device, it is preferred that at least some of said electrical connections have been formed in situ within said device.

DETAILED DESCRIPTION OF THE INVENTION

Figure 1:
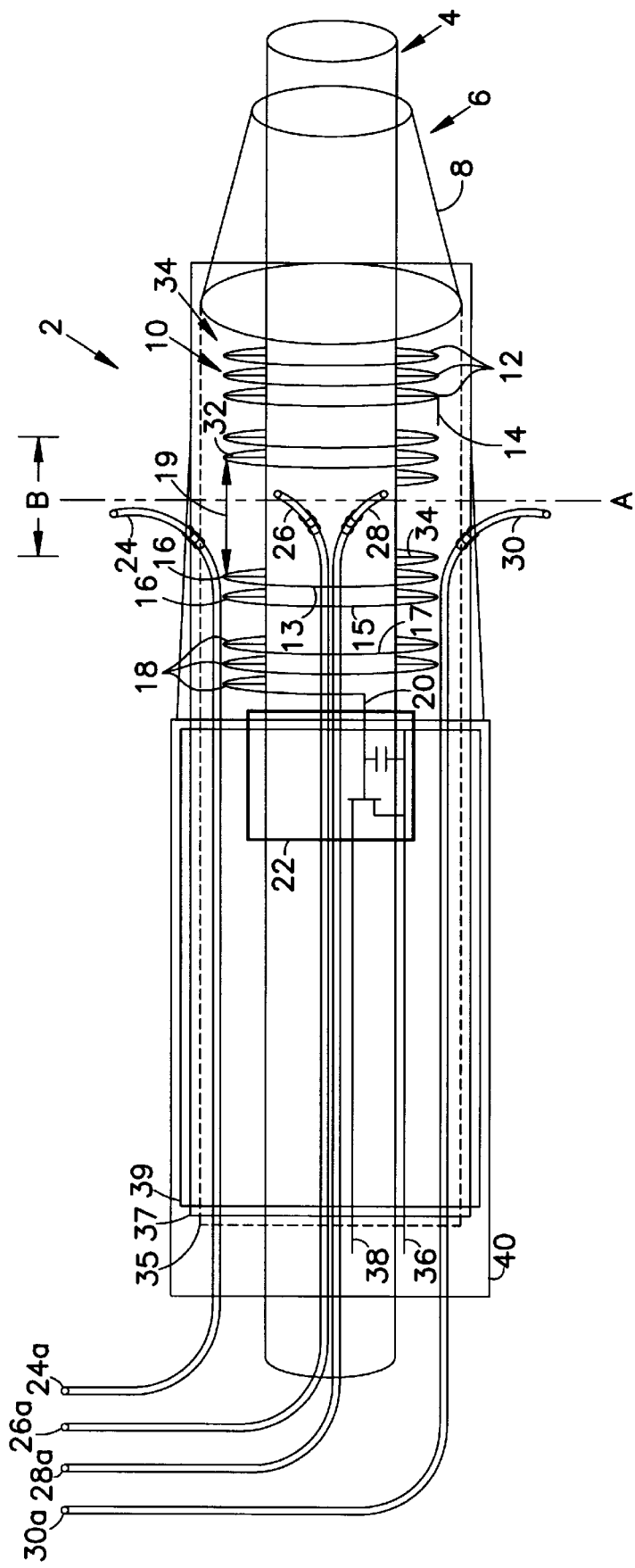
FIG. 1 shows a drug delivery catheter according to a practice of the present invention.

In the following detailed description of the preferred embodiments, references made to the accompanying drawings which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that structural, logical, physical, architectural, and electrical changes may be made without departing from the spirit and scope of the present invention. The following detailed description is, therefore, not to be taken in a limiting sense and the scope of the present invention is defined only by the appended claims and their equivalents.

The practice of certain aspects of the present invention are applicable to all medical devices which might be used with magnetic resonance imaging viewing procedures occurring concurrently with the primary medical procedure. Features of the present invention which may individually have this general applicability within the medical device field include the types of RF-responsive coils provided to medical devices to assure their MR-compatibility, circuitry associated with the devices, and means for directing microelements/microcatheter components and the like within a catheter device. The preferred construction uses an opposed solenoid orientation of microcoils with the microcoil design based on two coaxial solenoids separated by a gap region and with the current driven in opposite directions across the two coils.

One individual aspect of the present invention is the use of an opposed pair(s) of microcoils to accurately define a field around the device carrying the pair(s) of coils. By an opposed pair of coils is meant coils in which the angle of their coiling or winding about an axis is different (in a positive or negative sense, either with positive degree rotation away from a line perpendicular to the surface or negative degree rotation away from the line) between two sets of coils (e.g., receiver coils), usually with the angles differing from a plane perpendicular to the axis of the object about which the coils are wound or formed by + degrees for one coil and – degrees for the other coil as measured from the plane. Other individual advances in the potential areas of practice of the present invention include the circuitry which is connected to the coils, its shielding within the device, and decoupling circuitry, associated with the wires to the coils. Little specificity has heretofore been provided within the actual design and engineering details of radio frequency detectable invasive medical devices which addresses a wide range of functional needs within the device. This invention provides a substantive advance in the design of such devices.

Another area of import to the present invention is the option of providing drug delivery microcatheters within the radio frequency detectable device, with the receiver coils being usable in a process for detecting the actual delivery and movement of drugs according to the invention described in copending U.S. patent application Ser. No. 08/857,043 filed on May 15, 1997 in the names of John Kucharczyk and Michael Moseley, bearing attorney's docket number SLWK 600.392US1.

FIG. 1 shows a preferred drug delivery catheter 2 according to the present invention. The catheter 2 comprises a central lumen 4 which exits through a port 6 in a tapered end 8 of the catheter 2. A first microcoil 10 is wrapped about the lumen 4 so that the individual coils 12 generally angle away from the tapered end 8. A lead wire 14 is connected to the first microcoil 12. A second microcoil 16 is wrapped about the lumen 4 and the individual coils 18 are generally angled towards the tapered end 8. This pair of first microcoil 10 (and 32, collectively referred to as 10) and second microcoil 16 (and 18, collectively referred to as 16) form an opposed pair of microcoils. The individual coils of 10 and 32 for the relatively proximal set of microcoils 10 and the individual coils 16 and 18 for the second microcoil 16 have opposite (positive versus negative) angles with respect to a plane A-B which would be perpendicular to the lumen 4, which effectively defines an axis for the catheter 2. Note that the pair of coils may have different spacing between adjacent coils, e.g., between 13 and 15, as compared top between 15 and 17). This difference in spacing will be discussed later. A lead wire 20 passes from the second microcoil 16 to electronic circuitry 22, as does the lead wire 14 from the first microcoil 10. There is a definite separation of space between the first microcoil 10 and the second microcoil 16 within which the RF responsive field (not shown) from the coils 10 16 is the largest. It is within the space B outside of the catheter 2 in a zone defined by the opposed ends 32 34 of the two microcoils 10 16 (respectively) where delivery of drug from microcatheters 24, 26, 28 and 30 would be most effectively observed.

The microcoils 10 and 16 are embedded in a support material 34 which may be a polymeric material, composite material, inorganic material (e.g., inorganic oxide) or the like. The composition of this material should be biocompatable, preferably a polymeric material such as a polyamide, polyester, poly(meth)acrylate, polyvinyl acetate, cellulose acetate, or other classes of organic polymers which are biocompatable. This support material 34 may also comprise the composition of the tapered end 8. Lead wires 36 and 38 leave the circuitry 22 for connections to outside controls and/or power sources. The ends 24a, 26a, 28a, and 30a of the microcatheters 24, 26, 28 and 30 are shown, without their connection to a delivery system or pump for provision of agents or drugs being shown.

The intermicrocoil spacing B (as opposed to the intramicrocoil spacing) between the opposed sets of microcoils will usually be optimized for each type of drug delivery or other type of procedure to be practiced by the MR-compatible device 2, whether a catheter or other device. The parameters which would be considered for optimization, particularly with respect to the location of the microcoils would include at least the diameter of the field from the coils which is desired, the strength of the field, the width of the field, the number of field locations (e.g., the number of pairs of opposed microcoils), the location of the pairs of microcoils with respect to the distal end of the catheter, the location of the microcoils with respect to the point of delivery of the agents or drugs, etc. These considerations would be in addition to such engineering and other design considerations such as the thickness and size of the coils, the composition of the coils, the location of the circuitry (within the catheter or connected to an external circuitry through leads), and the composition of the other materials within the catheter construction.

Within said catheter construction at the more proximal end (away from the tip) may be a plastic layer 35 (which here is shown as a continuation of layer 8), a second insulating (e.g., plastic, ceramic, or biocompatible material as with the previous description of the support material for in layer 34) layer 37 which covers and electrically insulates the leads (wires) 36 and 38, and any preamplifier which may be present associated with the microcoils, from the shielding 39 which may form a layer around (radially away from) the leads 36 and 38 and/or preamplifier.

Intracoil spacing and intramicrocoil considerations (which overlaps intercoil and intermicrocoil considerations, as with respect to coil diameters) should also be considered in optimizing the design of the systems of the present invention.

Coils, particularly coils such as intra-vascular RF coil in MRI, can be very useful for MR imaging of vascular lumen morphology at a reduced field of view (FOV) with a high signal to noise ratio and spatial resolution. The most promising fundamental coil design for this type of purpose is a previously published (Martin, supra) opposed solenoid coil. The reported coils are two uniformly wound solenoids of an identical geometry and uniform coil diameter placed along a common axis with a reversed polarity. That particular coil design leaves a lot of room for improvement, based upon considerations not disclosed in the reference. One basis for improvement of the functional characteristics of the signaling is that a better intra-vascular coil can be obtained with a proper optimization for the current distribution within the coils. To optimize the current distribution on the surface of the cylinder (e.g., assuming a cylindrical shape for the underlying device, such as the catheter) with respect to a set of required field constraints, an analytical formulation for the magnetic field external to a cylindrical coil has been developed and is to be preferably used for our new coil design. Such an optimized coil yields an improved field strength and field uniformity. The uniform field strength is particularly important as certain methods of use of the devices of the invention use density readings and differentiations to generate the images or provide specific types pf information within the image (e.g., the rate of delivery of a drug or the degree of effect of a treatment represented by differences in signal density).

The geometry of the RF coil is, for the present analysis, based upon a small cylinder of a finite length. The current density is confined on the surface of the cylinder in the coils. Solving an appropriate static magnetic field problem for the geometry, for a cylinder shaped coil of radius a, the radial components of the magnetic field outside of the RF coil (>a) is given as $$B_r(\rho, z, \phi) = i\frac{\mu_0 a}{2\pi} \int_{-\infty}^{+\infty} J_\phi(0, k) k K_0'(k\rho) I_0'(ka) e^{+ikz} dk$$

where $J_\phi(m,k)$ denotes the azimuthal component of the surface current density in the expression above defined as $$J_\phi(m, k) = \frac{1}{2\pi} \int_0^{2\pi} d\phi e^{-im\phi} \int_{-\infty}^{+\infty} dz J_\phi(\phi, z) e^{-ikz}$$

and $I_m(t)$ and $K_m(t)$ denote two kinds of modified Bessel functions of mth order, wherein m denotes an integer (e.g., 1, 2, 3, . . . ), and $I'_m(t)$ and $K'_m(t)$ represent a first order derivative of $I_m(t)$ and $K_m(t)$.

The stored magnetic energy associated with the coil is found and given analytically in a form of series expansion as $$W = -\frac{\mu_0 a^2}{2} \sum_{m=-\infty}^{+\infty} \int_{-\infty}^{+\infty} |J_\phi(m, k)|^2 K'_m(ka) I'_m(ka) dk$$

Specifically for a solenoid coil or a z-coil in which the surface current density has no z-component, these expressions for both energy and field are simplified as:

$$W = -\frac{\mu_0 a^2}{2} \int_{-\infty}^{+\infty} |J_\phi(0, k)|^2 K'_0(ka) I'_0(ka) dk$$

$$B_r(\rho, z, \phi) = i\frac{\mu_0 a}{2\pi} \int_{-\infty}^{+\infty} J_\phi(0, k) k K'_0(k\rho) I'_0(ka) e^{+ikz} dk$$

To seek an optimal (or energy minimum) solution for current density distribution on the surface of the cylinder satisfying a set of the field constraints at some spatial locations, an energy functional construction is defined as follows, $$F = W - \sum_j \lambda_j (B_\rho(r_j) - B_j)$$

$$= -\frac{\mu_0 a^2}{2} \int_{-\infty}^{+\infty} |J_\phi(0, k)|^2 K'_0(ka) I'_0(ka) dk -$$

$$\sum_j \lambda_j \left[ i\frac{\mu_0 a}{2\pi} \int_{-\infty}^{+\infty} J_\phi(0, k) k K'_0(k\rho_{0j}) I'_0(ka) e^{+ikz_j} dk - B_j \right]$$

where represents a set of L multipliers. The field constraints specify a set of desired field values at a few points over an imaging volume of interest.

Minimizing the energy functional with respect to the current density functional, the variation with respect to the current density functional is performed:

$$\frac{\delta F}{\delta J} = \frac{\delta W}{\delta J} 0 - \sum_j \lambda_j \frac{\delta B_\rho(r_j)}{\delta J}$$

$$= -\frac{\mu_0 a^2}{2} 2 J_\phi(0, k) K'_0(ka) I'_0(ka) -$$

$$\sum_j \lambda_j i\frac{\mu_0 a}{2\pi} k K'_0(k\rho_j) I'_0(ka) e^{-ikz_j}$$

Then, the optimized current density is expressed in terms of the L-multipliers as, $$J_\phi(0, k) = -i \sum_j \lambda_j \frac{k}{2\pi a} \frac{K'_0(k\rho_j)}{K'_0(ka)} e^{ikz_j}$$

Since $J_\phi(z)$ will be antisymmetric in z for the desired field distribution, then its Fourier component can be expressed as $$J_\phi(0, k) = i \int_{-\infty}^{+\infty} dz J_\phi(0, z) \sin(kz)$$

inserting the expression for current density into the field constraint equations, a set of linear equation for the multipliers λ can be obtained:

$$B_{\rho m} = \frac{\mu_0}{4\pi^2} \sum_n \lambda_n \int_{-\infty}^{+\infty} \cos(kz_m)\cos(kz_m) \frac{K'_0(k\rho_n)}{K'_0(ka)} k K'_0(k\rho_m) I'_0(ka) dk$$

Solving the linear field constraint equations for the Langrange multipliers, then the current density can be determined from the expression involving these Langrange multipliers. For an RF coil of finite length (L), the surface current density can be expanded in terms of a sine series to a desired order, $$J_\phi(z) = \sum_{n=0} J_N \sin\left(\frac{2n\pi z}{L}\right) = \sum_{n=1}^N J_n \sin(k_n z)$$

$$J_\phi(k) = i \int_{-\infty}^{+\infty} dz J_\phi(z) \sin(kz)$$

where the value of $k_n$ is $$k_n = \frac{2\pi n}{L}$$

and $J_n$ denotes a set of expansion coefficients for the current density.

Then the general expression in k-space for the surface current density for the finite length coil can be written as:

$$J_\phi(k) = \int_{-\infty}^{+\infty} dz \sum_{n=0} J_n \sin\left(\frac{2n\pi z}{L}\right) e^{ikz}$$

$$= \frac{L}{2} \sum_{n=0} J_n \Psi_n(k)$$

where $\Psi_n(k)$ is an odd function in k, which is defined as $$\Psi_n(k) = \frac{\sin[(k+k_n)L/2]}{[(k+k_n)L/2]} - \frac{\sin[(k-k_n)L/2]}{[(k-k_n)L/2]}$$

Using the new function expansion, the corresponding expressions for stored magnetic energy and field can be written as $$W = -\frac{\mu_0 a^2}{2} \int_{-\infty}^{+\infty} \left|\frac{L}{2} \sum_{n=0} J_n \Psi_n(k)\right|^2 K'_0(ka) I'_0(ka) dk$$

$$= -\frac{\mu_0 a^2}{2} \left(\frac{L}{2}\right)^2 \sum_{m,n=0} J_m J_n \int_{-\infty}^{+\infty} \Psi_m(k) \Psi_n(k) K'_0(ka) I'_0(ka) dk$$

$$B_r(\rho, z, \phi) = \frac{\mu_0 a}{2\pi} \left(\frac{L}{2}\right) \sum_n J_n \int_{-\infty}^{+\infty} \Psi_n(k) k K'_0(k\rho) I'_0(ka) \cos(kz) dk$$

The desired reception field distribution external to a coil can be translated into a few field constraint points at some selected locations. For each particular design, these field constraint points are defined as:

z=0.000 p=b B=1.0
z=0.005 p=b B=0.8

The constraints specify a required field homogeneity of the coil at the gap as well as the relative field strength. The field constraint equations for radial component at various points of interests can be represented as follows $$B_r(\rho_j, z_j) = \sum_n J_n b_{nj}$$

$$= \frac{\mu_0 a}{2\pi}\left(\frac{L}{2}\right)\sum_n J_n \int_{-\infty}^{+\infty} \Psi_n(k) k K'_0(k\rho_j) I'_0(ka) k z_j dk$$

For convenience, both field and energy expressions are expressed in matrix form. Among the two, the matrix elements for b are given as $$b_{nj} = \frac{\mu_0 a}{2\pi}\left(\frac{L}{2}\right)\int_{-\infty}^{+\infty} \Psi_n(k) k K'_0(k\rho_j) I'_0(ka) \cos(kz_j) dk$$

The magnetic stored energy in the coil is $$W = -\frac{1}{2}\mu_0 a\left(\frac{L}{2}\right)^2 \sum_{mn} J_m J_n \int_{-\infty}^{+\infty} \Psi_m(k)\Psi_n(k) K'_0(ka) I'_0(ka) dk$$

$$= -\frac{1}{2}\sum_{mn} J_m J_n W_{mn}$$

where the energy matrix elements are given by $$W_{mn} = -\mu_0 a\left(\frac{L}{2}\right)^2 \int_{-\infty}^{+\infty} \Psi_m(k)\Psi_n(k) K'_0(ka) I'_0(ka) dk$$

The energy functional involving the field constraints equation is defined as $$F = W - \lambda^T(b^T J - B^0) = \frac{1}{2} J^T W J - \lambda^T(b^T J - B^0)$$

To seek the minimum condition of the energy functional, the F functional is minimized with respect to the current column vector J, i.e., $$\frac{\partial F}{\partial J} = J^T W - \lambda^T b^T = 0$$

then we arrive the following minimum condition equation involving the current density, $$WJ = b\lambda \qquad J = W^{-1}b$$

Using the field constraint equation as another independent equation:

$$b^T J = B^0$$

First, the Lagrange multipliers can be solved in the following linear equation, which combines both minimum condition and field constraint equations above.

$$b^T W^{-1} b\lambda = B^0$$

Using these values for these Lagrange multipliers, the surface current density for the coil can be uniquely determined as $$J = W^{-1}b\lambda$$

and then the current density is $$J_\phi(z) = \sum_{n=1}^{N} J_n \sin(k_n z)$$

The total current for one half of the coil is given by $$I_{total} = \int_0^{L/2} J_\phi(z) dz = \sum_{n=1}^{N} J_n \frac{1-(-1)^n}{k_n}$$

If the number of turns is set to $N_{turn}$, the individual current can be determined as $$I = \frac{I_{total}}{N_{turn}}$$

The inductance of the coil with N turns on one half of the coil is, $$L_{inductance} = \frac{2W}{I^2}$$

To determine the position for each current loop, the following integration of the current density is computed from the center of the coil, $$I_{total}(z) = \int_0^z J_\phi(z') dz' = \sum_{n=1}^{N} J_n \frac{1-\cos(k_n z)}{k_n}$$

This integration allow the finding of all the spatial intervals for a total of N different discrete current wire loops. The exact location of each wire along the z-axis can be determined as the center of mass over the corresponding interval.

$$z = \frac{\int_{z^-}^{z^+} z J_\phi(z') dz'}{\int_{z^-}^{z^+} J_\phi(z') dz'}$$

In conclusion, a means for optimization of the intracoil distribution of coils within each microcoil in an opposed pair of microcoils may be based on these or alternative mathematic modeling of the effects of current, coil properties, and individual coil or winding positioning and design. This particular scheme has been developed for a cylindrical shaped RF coil, the technique allowing a straight forward procedure in performing a design optimization for the current loop positions of an intravascular, intracavitary, intraparenchymal, or intraluminary MR imaging coil.

Figure 4A:
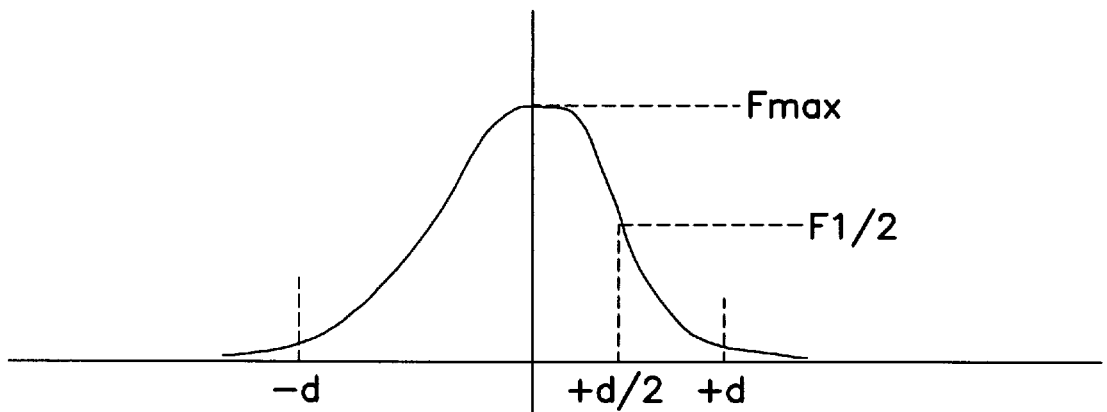
FIGS. 4a, b, and c shows graphic respresentations of Field Strength versus distance from the center of the gap between two opposed pairs of microcoils for three microcoil structures.
Figure 4B:
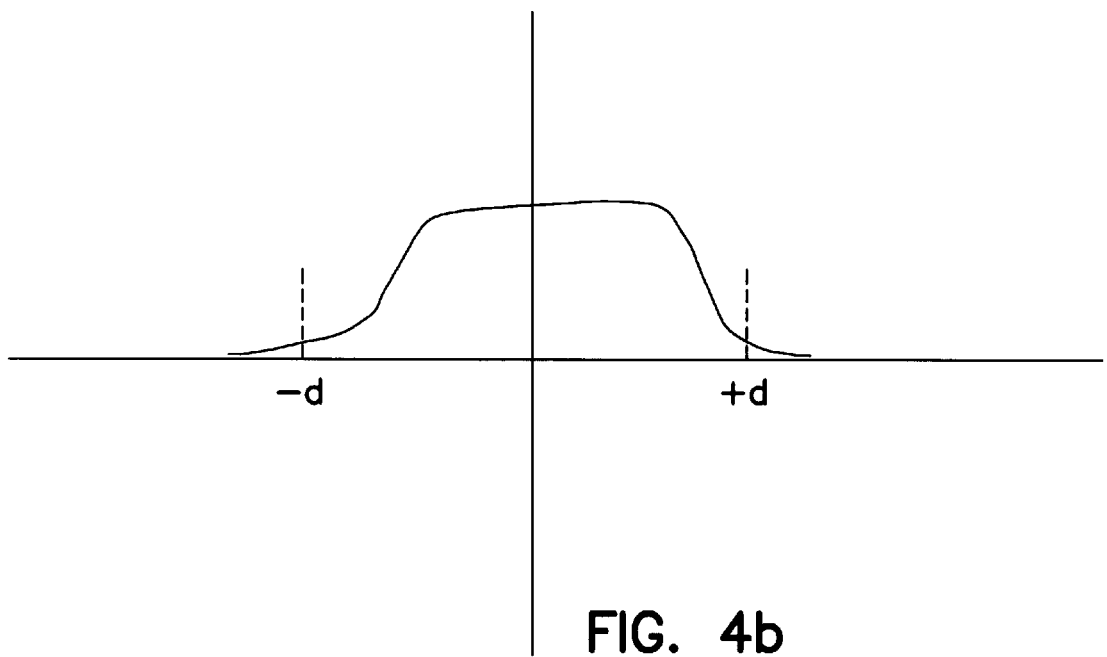
Figure 4C:
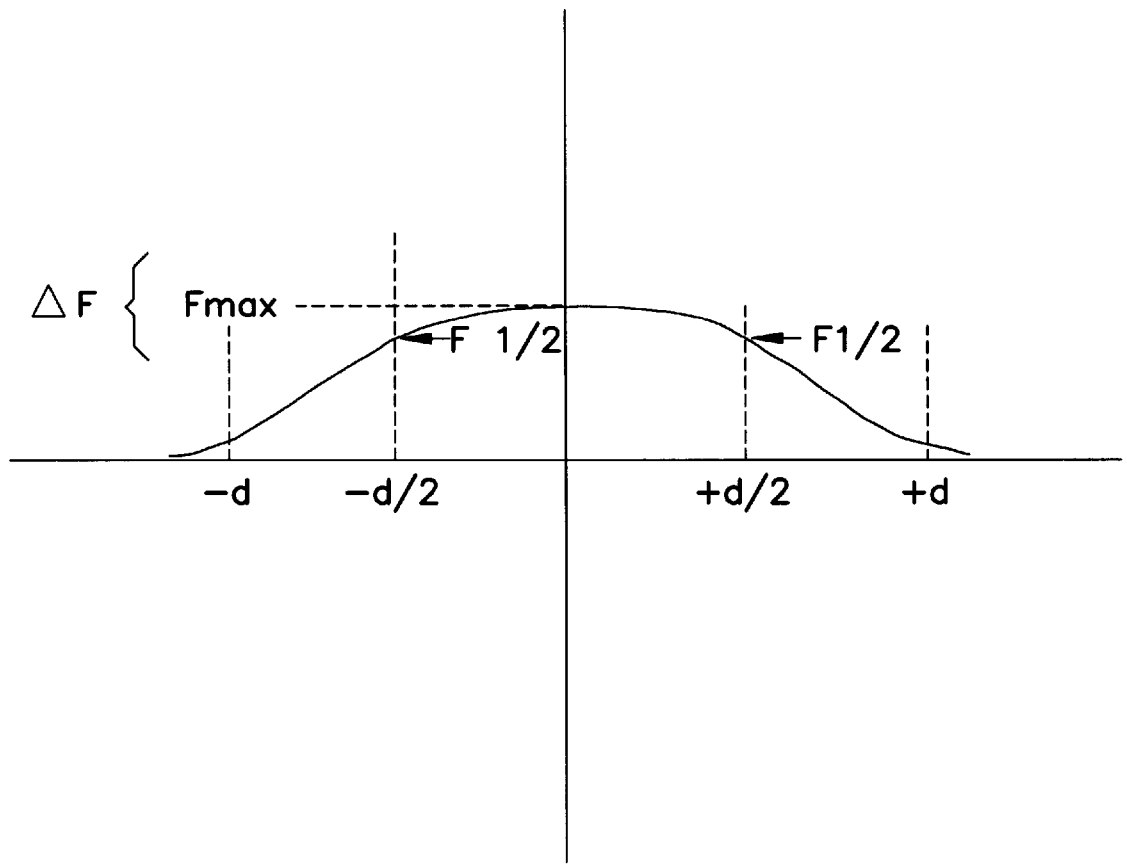

Reference to FIGS. 4(a, b and c) will help to explain the way in which modification of intracoil design can benefit performance of the catheters of the present invention. FIG. 4a shows the Field Strength (y axis) as a function of distance away from a central point in the gap (e.g., midway between nearest ends of opposed microcoils separated by a distance of 2d, as represented by space 19 in FIG. 1). FIG. 4a shows the Field Strength relationship in a cylindrical device having an opposed pair of microcoils with equal size of the individual windings and equal spacing between each of the windings. As can be noted from FIG. 4a, the maximum field strength Fmax is a relatively sharp peak, and the field strength diminishes as the distance from the center of the gap (x=0) changes. At a point halfway between the middle of the gap (with a dimension of d from ends of the opposed microcoils closest to each other) and the ends of the opposed microcoils, the field strength will drop off significantly, typically between 25 and 50% of Fmax. This rapid and significant change in the field strength can reduce the capability of the device in providing the type and quality of image in certain procedures. FIG. 4b shows an idealized version of a field strength distribution which can be provided with design considerations of the location, shape, thickness and distribution of the microcoils according to the modeling considerations discussed above. The effects of each individual winding contribution can be calculated mathematically as shown above, and then the individual contributions added together to determine the effective field strength. Some interactive effects may be considered in the mathematic summation of individual winding effects, to match the more realistic field effects from the combination of coils. A more attainable field strength distribution is shown in FIG. 4c, where a less idealized, but significantly improved field strength distribution is shown. FIG. 4c shows the relationship of field strength and position along the cylindrical device where the device has an opposed pair of microcoils with a spacing of 2d between the near ends of the opposed pairs of coils (as shown as 19 in FIG. 1) which has the sections of windings of the coils (in FIG. 1, e.g., 13, 15 and 17) differentially spaced (e.g., different spacing between windings 13 and 15 as compared to the spacing between 15 and 17 on the same microcoil). The field strength is more uniform near the center of the gap (where x=0) as compared to the opposed microcoil structure whose field strength is shown in FIG. 4a. The field strength does diminish as the distance from the center of the gap increases, but the diminution rate is less than that for the uniform coil windings of FIG. 4a, although less than that for the idealized results of 4b. The field strength can be expected to drop less than 20% between the center of the gap and a position d/2 which is one half the distance from the center of the gap to the near end of a microcoil. It is preferred that the field strength diminish less than 17%, more preferably less than 15%, still more preferably less than 12%, and most preferably less than 10 or less than 8% between the Fmax and the field strength at the d/2 point, midway between the center of the gap and a near end of the microcoil.

A device according to the present invention may also be described as a medical device for use within an organism, said medical device comprising an element having at least one pair of opposed RF receiver microcoils having a space between each microcoil of said pair of microcoils, said RF receiver microcoils each comprising at least three individual coils, said at least three individual coils of said microcoils having spacing between adjacent microcoils so that spacing between at least two pairs of individual coils within said microcoils differ by at least 10%. The spacing between pairs of the individual coils (or windings) as measured along a line within the plane within which the microcoils reside and parallel to the axis of the cylinder (or other shape) on which the surface lies may be at least 12%, at least 15% or at least 20% or more, as compared to other spacings between adjacent windings to effect improved results in the field strength distribution within the gap.

Another design configuration which is allowable in the structures useful in the practice of the present invention is to have two layers of microcoils within the region defining one half of a pair of microcoils. That is, a first set of microcoils angled towards the gap may be located within one layer of the MR observable device, and a second set of microcoils (e.g., a set of windings) also may be angled towards the gap, but be located within an insulated layer overlaying or underlying the first set of microcoils. The spacing between coils in the sets of similarly angled microcoils may be of the same or different thickness, the same or different spacing between coils, and/or the same or different angles (although they both must be angled towards or both be angled away from the gap). The device may have at least one set of microcoils wherein a half of said at least one pair of microcoils comprises at least four windings having at least three spaces between adjacent windings of dimensions space 1, space 2 and space 3, wherein at least one of said at least three spaces does not equal the dimensions of at least one other of said spaces.

Many available technologies and structural considerations known in the art may be included within the practice of the present invention, even if some of these considerations are used within the novel structural designs of the present invention. For example, the composition of the lumen 4, support material 34, and catheter casing 40 may be selected from amongst known biocompatable materials which have been developed for medical uses. The microcoils and circuitry forming a part of the catheter system may be provided by known techniques, even if those techniques have not heretofore been used within the medical device field. For example, the microcoils could be provided by wrapping filament of conductive material (especially copper, copper coated materials, and other RF antenna materials known in the art) or by forming the filaments on or over the lumen. Such forming processes would include deposition processes, growth deposition processes, deposition and etching processes, microlithography, masked deposition, and the like. The deposition processes may include such varied technologies such as plating, electroless plating, sputtering, seeded growth, (e.g., U.S. Pat. Nos. 4,775,556 and 4,710, 403), high energy deposition or etching processes (e.g., U.S. Pat. Nos. 5,389,195 and 5,332,625), chemical deposition and etching processes, etc. The techniques for providing circuitry and wiring shown in U.S. Pat. Nos. 5,106,455; 5,167,625; and 5,269,882 are examples of other technologies generally useful in the deposition of circuitry on filamentary articles and surfaces.

Figure 2:
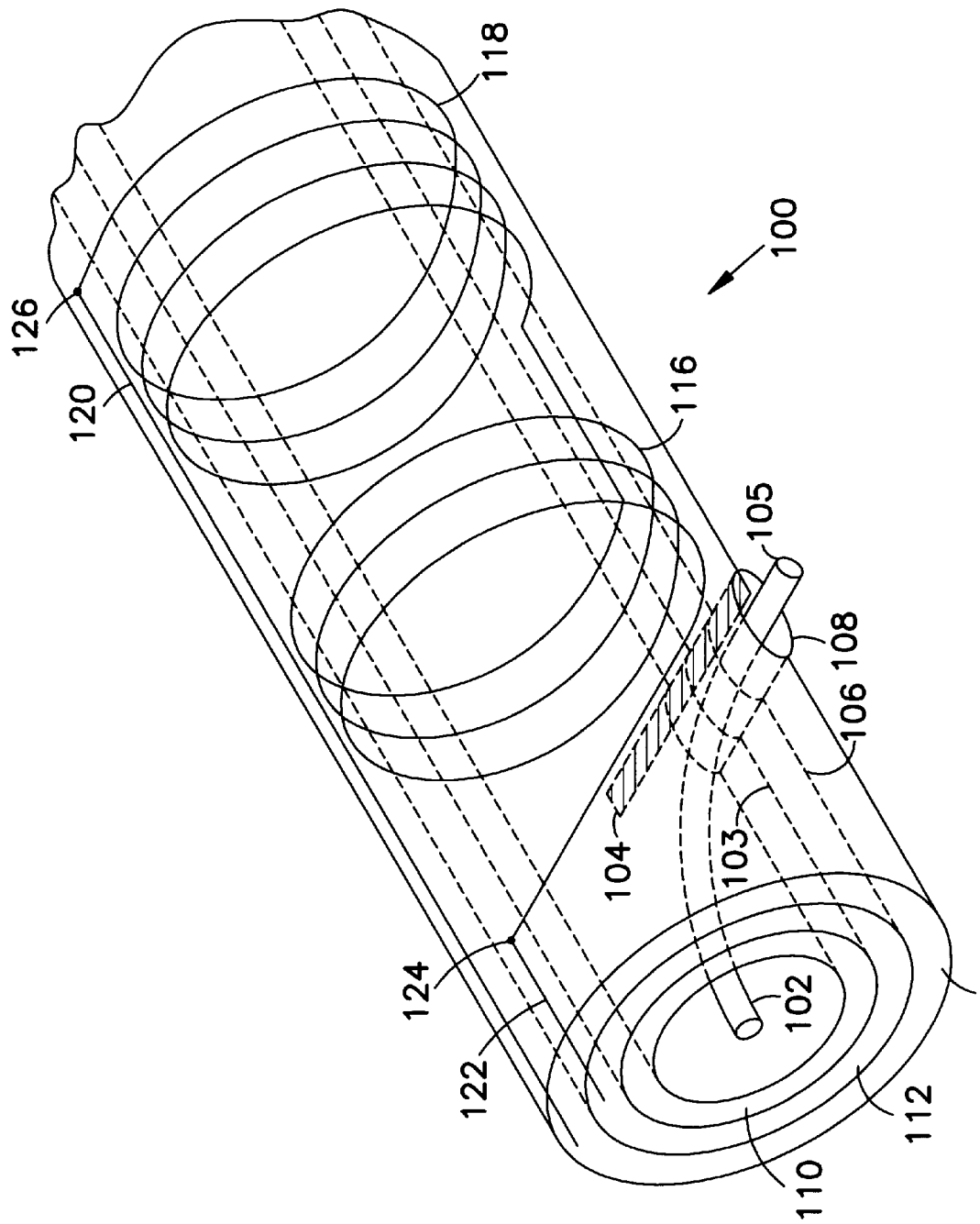
FIG. 2 shows a sectional view of a catheter emphasizing microcatheter exits on the catheter and wiring on the catheter.

FIG. 2 shows a sectional view of a mid-range portion of a catheter 100 according to one configuration which may be used in the present invention. A microcatheter 102 is shown to have been deflected against an internal guiding element or deflector 106 so that an end 105 of the microcatheter 102 extends out of the catheter 100 through a hole 108 in the walls of the catheter 100. The microcatheter 102 has been deflected by the deflector 104 and rests against the deflector 104 beginning at a contact point 103. The hole 108 passes through what is shown in this FIG. 2 as three layers 110, 112 and 114 of material making up the substantive walls of the catheter 100. The deflector 104 helps to guide the microcatheter 100 into and through the hole 108. There would be a hole and deflector for each microcatheter which exits from the catheter (and these microcatheters may be provided with their own intrinsic microcoils) and these microcatheters (not shown) exits from the catheter 100, unless two or more microcatheters were to exit from a single hole, which is not a preferred construction simply for the reason that this would cause a major portion of the effects of the microcatheter (e.g., drug delivery) to occur in a limited area with respect to the surface of the catheter 100. The device may have at least three deflectors for directing each of at least three microcatheters through at least three distinct ports.

Also shown in FIG. 2 are a pair of microcoils 116 and 118. These microcoils 116 and 118 have been shown to be embedded within layer 112 of the catheter 100. It is highly desirable for optimal performance of the imaging and location function of the catheter 100 that signal produced by the microcoils 116 and 118 be as precise and clear as possible. The presence of other circuitry and wires within the catheter can interfere with this type of performance, and so special considerations should be taken to avoid any interference problems with the electrical and electronic functions of the various parts of the catheter and its subcomponents. For example, the wires 120 and 122 which are connected to ends 124 and 126 of the microcoils 116 and 118, respectively, must not contact the microcoils 116 and 118 except where they are intended to be electrically connected thereto (e.g., at ends 124 and 126). This can be accomplished in a number of different ways according to the practice of the present invention. There is less structural potential for problems of this type with the proximal microcoil 116, because its end 124 may be connected to a wire 122 and not pass over the coil circuitry. The wire 122 may therefore be located within the same layer 112 as the coil 116. With the distal microcoil 118, the wire 120 must pass back over both coils 116 and 118 and could contact or otherwise readily interfere with any signal coming from the microcoils 16 and 118. To prevent this, the microcoils 116 and 118 are shown within a single layer 112, but the wire 120 from the distal microcoil 118 is shown within layer 124 to reduce or eliminate any electrical or electronic interference or interaction with the coils 16 and 118 or other circuitry (not shown) in the catheter 100. The separation of these respective elements into separate layers can be accomplished according to numerous techniques available within the general manufacturing art once the need has been recognized for the appropriate location of the elements. For example, once microcoils have been laid down (by wrapping, deposition or etching, for example), a polymer or other insulating material may enclose the microcoils in a distinct layer (e.g., layer 112). Once this protective or enclosing layer has been established (with appropriate electrical connection points maintained for other electrical or electronic connections), the other wiring or circuitry may be then constructed on that covering enclosing layer (e.g., 112). This additional wiring or circuitry may be constructed by processes similar to those processes used to make the coils or other processes known to those skilled in the art, including wrapping, gross application of premade circuitry, deposition of circuit or wire elements, etching of circuits or wire elements, and other construction or microconstruction techniques known in the art. A main objective of this optional structure within the practice of certain constructions of the present invention is to provide circuitry and/or wiring within distinct layers (even if of the same polymer binder composition) of the catheter. The location of the wiring or additional circuitry is done with an intent to minimize crosstalk, interference, interaction or other related effects which could be detrimental to the performance of the microcoils and circuitry. Specific interactive wave effects or field effects could be considered in the design of the location of the respective elements in performing these considerations.

A composite catheter for MR image monitored drug delivery according to certain aspects of the present invention may concern a composite device (needle or catheter) or other with a built in micro-imaging coil for MR imaging (spectroscopy) monitoring or other physiological monitoring during a therapeutic procedure. The micro coil can be interfaced to a conventional MR scanner to image the pathological change of the region at immediate proximity to the coil as well as the therapeutic site with a very high signal to noise ratio without interrupting the drug delivering process. These types of devices will become highly desirable in the near future for many neurological transparenchymal or endovascularly therapeutic applications.

One of the composite devices is shown schematically in FIG. 1. As illustrated in FIG. 1, the catheter has a number of micro size tubes 24, 26, 28 and 30 in the lumen 4 for performing various functions such as physiologic measurements, drug delivery, material withdrawal, sampling, temperature moderation or alteration, electrical stimulation, and the like. At the tip of the catheter, there exists a micro coil 10 along with a micro sized pre-amplification unit 22 for MR imaging and spectroscopy.

In general, such a composite device (or catheter) includes at least a micro-imaging coil which can be broken down into four modular parts as shown in FIG. 2:

1). Optimized imaging coil or electrode
2). Pre-amplification and decoupling integrated circuit
3). Signal transmission and shielding
4). Remote matching circuit.

Although these four parts are not necessarily separated from each other for a specific composite device design, the separation of modules are only meant for the ease of the following description.

In most cases, some of these modules are often integrated into one composite unit. The micro coil for MR imaging can be one of the following: a single loop, twisted wires, two opposed solenoids. All of these coil designs are extremely sensitive to the immediate region close to them. The detailed spatial sensitivity profile of a specific coil depends on its conductor pattern.

For the opposed solenoids, the primary magnetic field flux for reception is squeezed out at the gap between the two coils (in a direction generally perpendicular to the windings and/or the axis of the cylindrical device around which the coils are wound or formed), the number of winding required is about at least about three, more preferably between three and twenty, still more preferably between 4 and 16 for each coil, and most preferably with 5 to 12 coils with a diameter of each coil on the order of 0.1 to 2.4 mm possible, more preferably diameters of 0.3 to 2.0 mm are used, and most preferably 0.5–2.0 mm diameters are used. By depositing the coils onto the surface, wider widths of the coils may be used with less volume being taken up by the coils, with thin layers of materials being deposited as the coils (e.g., with thicknesses of a few microns being possible, up to thicknesses equal to the width of the coils) depending on the size of the catheter. Although the coil is wound or deposited on a cylindrical surface of a small diameter, there exist some degrees of freedom for optimization. For the solenoid coil design, one of the degrees of freedom is the spacing between the windings. To a certain extent, the design of the micro size coil can be numerically optimized for producing a desirable reception field pattern (uniformity) in space under the geometric shape constraint imposed by a given clinical device. Using a target field method, the conductor pattern can be numerically optimized to closely match any targeted reception field pattern. The coils within the microcoils may be formed or wound with spacing of from 2.0 coil diameters between centers of adjacent coils (so that the spacing between outer sides of adjacent coils is equal to the diameters of the individual coils) up to 10 coil diameters between centers of adjacent coils (so that the spacing between outer sides of adjacent coils is equal to nine diameters of the individual coils). Preferably the spacing is between 2.5 and 8 diameters, more preferably between 3 and 6 diameters. As noted earlier, the prior art has suggested that the use of microcoils with diameters of less than 2.8 mm is undesirable. Where the coils are opposed and angled, it is desirable in the practice of the present invention to have the coil diameters less than or equal to 2.4 mm. It is also novel in the present invention to provide the microcoils with different intracoil spacing within each half of the coil pairs and to have the coil dimensions greater than the preferred 2.4 mm and less. For example, the coils could easily be up to and including 4.0 mm, up to 3.5 mm, up to 3.0 mm and the like, inclusive of the preferred lower dimensions where the intracoil spacing is varied according to the teachings of the present invention.

Furthermore, the material for the wire of coil can be any non-magnetic metal or metal alloys with a similar magnetic susceptibility as that of the human tissue. For example, the preferred materials can be simply copper, silver, Al and copper-Al composite. Both copper and silver are diamagnetic, and Al is paramagnetic. For minimizing the field disturbance, the coil conductor wire can be made to have multiple concentric layers of different metallic materials ($Cu_\chi = -9.7 \times 10^{-6}$ and $Al_\chi = +20.7 \times 10^{-6}$). The exact layer thickness or radius for different metal components can be numerically optimized for different size of the wires. For a zero susceptibility cylindrical shaped wire, the ratio of the radii is given by $$\frac{r_{out}}{r_{in}} = \sqrt{\frac{\chi_{out} - \chi_{in}}{\chi_{out}}}$$

Figure 3A:
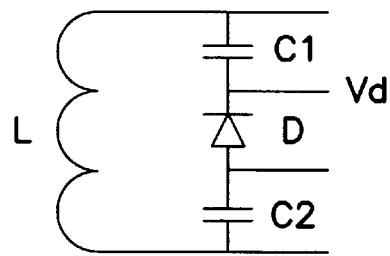
FIGS. 3a and 3b show schematic representations of circuitry for the catheter of the present invention.
Figure 3B:
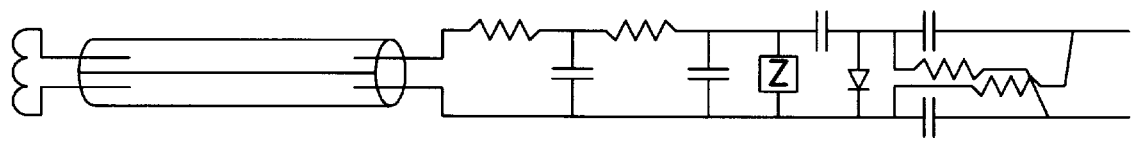

To minimize the mutual coupling between the microcoil and the volume coil used for image excitation, a decoupling circuit is preferably incorporated on the micro coil. During the excitation, such decoupling circuit element makes the micro coil invisible to the volume coil by detuning the resonant frequency of the imaging coil away from the transmitting RF frequency. One of the designs accomplishing the coil decoupling requirement is shown in FIG. 3. Where the unit includes a PIN diode denoted by D in series with the two capacitors (C1 and C2), the image coil is shown symbolically and denoted by L. The PIN diode D can be actively switched on and off by an external control voltage Vd across the diode. When the diode D is switched on, the coil L and two capacitors C1 C2 form a resonant circuit tuned to the frequency. This is an improved version of the circuitry including a pre-amplification unit. The unit also may include a PIN diode denoted in series with only one capacitor, the diode can be actively switched on and off by an external control voltage. An FET (denoting a field effect transistor) may be provided for signal amplification at RF frequency. To protect the FET component or any other type of pre-amplification module during the RF excitation, a crossed diode can be placed in front of the FET, bypassing excess induced current during RF transmission.

The entire coil can be a composite. In another words, the entire imaging coil can be made of multiple coil elements connected in series or in a phased array fashion for simultaneously imaging at multiple locations along a catheter. All of these multiple coils can be similar or different in their geometrical shape. The imaging coil can also be non-local. That is, the coil can be spatially distributed along a significant length of a catheter (especially by consideration of modeling as shown above). For this purpose, there are many choices for the active coil components: twisted wire, two parallel wire, coaxial cable, combinations of these, etc.

In addition to the variety available in the selection of the imaging coil component, various other components, such as micro electrodes can be incorporated in the device for the cell or membrane potential measurement, pressure/flow monitoring or other physiological monitoring.

For optimal signal to noise ratio (S/N) or minimal resulting noise figure, the MR signal detected would preferably have an immediate amplification (e.g., preamplification) in a location as close as possible to the coil element. The practical catheter geometry does not provide enough room for using any conventional amplification components. For the purpose of minimizing the size of the electronic components which will be used for various signal preconditioning such as pre-amplification, we have introduced an integrated circuit module in close proximity to the imaging module. The integrated circuit module includes a pre-amplification device (or unit at RF frequency ) and other auxiliary devices fabricated on a silicon chip, which is preferably less than 4 $mm^2$ in size. The same integrated circuit module is preferred to be packaged in a small non-magnetic casing compatible in shape with a given instrument design. One of the most simple units may contain only a single FET element. With the help of the integrated circuit technology, more elements can be incorporated into one single silicon module for building more complex circuitry to achieve a better performance.

The preferred transmission module is a portion of the flexible cable along the catheter for transmitting the RF signal detected for MR imaging from the coil to a remote terminal for further signal amplification and other required processing. In preferred design contemplations, all of the components of the cable are integrated to the catheter. One of the desired requirements for the cable is that it will introduce a minimal noise contamination as well as a low signal attenuation to the minute MR signal. The other desired requirement for the cable is that it will introduce a minimal hindrance to the flexibility and the stiffness of a catheter. For achieving these requirements, there are a number of the possible alternatives for the device as follows:

1) A tri-coaxial cable (a cable with a center line conductor surrounded by two concentric layers of shielding material). One variation of the cable is that the center conductor is wound in a helical fashion along the center axis of the cable.

2) A shielded twisted wire cable ( a cable with two twisted wires at the center surrounded by a concentric layer of shielding material). One variation of the cable is that the two wires are wound in a spiral or helical fashion along the center axis of the cable.

3) A shielded parallel bi-polar cable ( a cable with two parallel bi-polar wires placed symmetrically with respect to the center axis surrounded by a concentric layer of shielding material). One variation of the cable is that the two wires parallelly are wound in a spiral or helical fashion along the center axis of the cable.

The shielding layer can be a layer of braided thin conductive wires as well as a layer of metallic film, or any other shielding material )which may be grounded if desired) as understood in the art which may be provided in a dimension compatible with the practice of the present invention.

Yet another useful design is a concept of putting all the elements at the remote unit (or distal end). The schematic circuit diagram shown above in FIG. 3 includes an imaging coil (micro or macro), transmission line, phase shift network, tuning and decoupling circuit and balun (i.e., balanced/unbalanced impedance matching transformer). The Z denotes a tuning element (L or C) as a part of decoupling circuit. The combined transmission line and phase shift network exhibits a quarter or half wavelength property.

The remote matching unit represents a device placed at the remote end of the device. This remote unit can be used as an extra tuning device for the imaging coil at the tip as well as a detuning (or decoupling) device. The remote match unit takes the effective impedance transformation of the transmission unit into consideration for the coil impedance matching and frequency tuning. In this design, both the transmission wire and the remote unit are used for accomplishing the tuning and detuning. In order to take advantage of the property of the transmission wire, the wire with a quarter wave or half wave length of the radio frequency if interest is used. Otherwise a transmission wire with a phase shift network which shows the same effective quarter wave or half wave length behavior can be used. The coil tuning can be accomplished with a capacitor or inductor. In addition, the size of the unit is not constrained geometrically. Since the device size for this module is not an issue, more conventional electronic components can be used. Depending on a specific design, the remote unit can be very important or of no importance.

Finally, the catheter tip has a stabilization mechanism incorporated. The preferred stabilization unit can be mechanically driven, or made of memory metal control with external applied voltage signal.

What is claimed is:

1. A medical device for use within a living organism, said medical device comprising: an element having at least one pair of opposed RF receiver microcoils having a space between each microcoil of said pair of microcoils, said RF receiver microcoils each comprising at least three individual windings, said at least three individual windings of said microcoils having spacing between adjacent windings so that spacing between at least two pairs of individual windings within said microcoils differ by at least 10%.

2. The medical device of claim 1 wherein at least one drug delivery port is present within said device and wherein said at least one drug delivery port is located so that at least some drug which is delivered through said port is delivered away from said device within a volume above said space between said individual microcoils of said at least one pair of microcoils.

3. The medical device of claim 2 wherein the windings of said microcoils have diameters of less than 2.4 mm.

4. The medical device of claim 1 wherein there are at least three separate ports within said device for delivery of drugs by at least three microcatheters within said device through said ports.

5. The medical device of claim 4 wherein within said device are at least three deflectors for directing each of said at least three microcatheters through said at least three ports.

6. The medical device of claim 1 wherein at least one set of microcoils comprising a half of said at least one pair of microcoils comprising at least four windings having at least three spaces between adjacent windings of dimensions spacing 1, spacing 2 and spacing three, wherein at least one of said at least three spaces does not equal the dimensions of at least one other of said spaces.

7. The medical device of claim 6 wherein a layer is present within said device which is radially exterior to a component selected from the group consisting of electrical wires and preamplifiers associated with said microcoils, said layer providing RF shielding for said electrical wires and/or any preamplifiers associated with said microcoils, and said layer being electrically insulated from components selected from the group consisting of electrical wires and preamplifiers associated with said microcoils.

8. A medical device for use within a living organism, said medical device comprising: an element having at least one pair of opposed RF receiver microcoils having a space between each microcoil of said pair of microcoils, said RF receiver microcoils each comprising at least three individual windings, said at least three individual windings of said microcoils having spacing between adjacent windings so that spacing between at least two pairs of individual windings within said microcoils differ by at least 10% wherein said at least one pair of RF receiver microcoils has a space between each half of said pair of microcoils, said at least one pair of RF receiver microcoils produces a field strength having a field strength maximum within a volume surrounding said space between each half of said pair of microcoils, and produces a second field strength at a position along a line parallel to an elongate axis of said device halfway between a midpoint position within said space and a near end of a microcoil forming a part of said at least one pair of RF receiver microcoils, said second field strength, along a line parallel to an elongate axis of said device, being no more than 40% less than said maximum field strength between said microcoils.

9. The medical device of claim 8 wherein said second field strength is no more than 20% less than said maximum field strength.

10. The medical device of claim 9 wherein the windings of said microcoils have diameters of less than 2.4 mm.

11. The medical device of claim 8 wherein the windings of said microcoils have diameters of less than 2.4 mm.

12. The device of claim 8 wherein at least one drug delivery port is present within said device and wherein said at least one drug delivery port is located so that at least some drug which is delivered through said port is delivered away from said device within a volume above said space between said individual microcoils of said at least one pair of microcoils.

13. A medical device for use within an organism, said medical device comprising: an element having at least one pair of opposed RF receiver microcoils having a space between each microcoil of said pair of microcoils, coils of said microcoils having diameters of less than 2.4 mm wherein at least one set of microcoils comprising a half of said at least one pair of microcoils comprises at least four windings having at least three spaces between adjacent windings of dimensions spacing 1, spacing 2 and spacing three, wherein at least one of said at least three spaces does not equal the dimensions of at least one other of said spaces.

14. The medical device of claim 13 comprising an element having at least one pair of opposed RF receiver microcoils comprising: at least three windings in each of said microcoils, said windings having a space between each winding of said pair of microcoils, the windings of said microcoils having diameters of less than 2.4 mm and said at least one pair of opposed RF receiver microcoils consisting of a continuous winding.

15. The medical device of claim 14 wherein at least one drug delivery port is present within said device.

16. The medical device of claim 15 wherein said at least one drug delivery port is located so that a drug which is delivered through said port is delivered away from said device within said space between said microcoils.

17. The medical device of claim 14 wherein microcatheters are present within said device which extend outside of said device to deliver liquid material within a volume bordered by planes extending radially from the catheter at ends of the at least one pair of microcoils which volume bordered by planes defines the space between each microcoil within said at least one pair of microcoils.

18. The medical device of claim 14 wherein said at least one pair of microcoils is embedded within a binder material which surrounds a lumen.

19. The medical device of claim 18 wherein said at least one pair of microcoils is electrically connected to a preamplifier within a portion of said device which may be inserted into an organism.

20. The medical device of claim 14 wherein said at least one pair of microcoils is electrically connected to a preamplifier within a portion of said device which may be inserted into an organism.

* * * * *